United States Patent
Kheiri et al.

(10) Patent No.: US 8,460,329 B2
(45) Date of Patent: Jun. 11, 2013

(54) SINGLE-PUNCTURE LANCING SYSTEM

(75) Inventors: Mohammad Kheiri, Elkhart, IN (US);
Weiping Zhong, Granger, IN (US);
Tieming Ruan, Granger, IN (US)

(73) Assignee: Bayer HealthCare LLC, Tarrytown, NY (US)

( * ) Notice: Subject to any disclaimer, the term of this patent is extended or adjusted under 35 U.S.C. 154(b) by 967 days.

(21) Appl. No.: 11/921,987

(22) PCT Filed: Jun. 29, 2006

(86) PCT No.: PCT/US2006/025695
§ 371 (c)(1),
(2), (4) Date: Dec. 10, 2007

(87) PCT Pub. No.: WO2007/005665
PCT Pub. Date: Jan. 11, 2007

(65) Prior Publication Data
US 2010/0217300 A1 Aug. 26, 2010

Related U.S. Application Data

(60) Provisional application No. 60/695,391, filed on Jun. 30, 2005.

(51) Int. Cl.
*A61B 17/32* (2006.01)
(52) U.S. Cl.
USPC .......................................................... 606/182
(58) Field of Classification Search
USPC ................................................. 606/182, 181
See application file for complete search history.

(56) References Cited

U.S. PATENT DOCUMENTS

| | | | |
|---|---|---|---|
| 4,203,446 A * | 5/1980 | Hofert et al. | 606/182 |
| 4,517,978 A | 5/1985 | Levin et al. | 128/314 |
| 4,677,979 A | 7/1987 | Burns | 128/314 |
| 5,954,738 A | 9/1999 | LeVaughn et al. | 606/181 |

(Continued)

FOREIGN PATENT DOCUMENTS

| EP | 0 115 388 A1 | 8/1984 |
|---|---|---|
| EP | 0 204 892 A2 | 12/1986 |

(Continued)

OTHER PUBLICATIONS

Written Opinion corresponding to International Patent Application Serial No. PCT/2006/025695, European Patent Office, dated Nov. 10, 2006, 5 pages.

(Continued)

*Primary Examiner* — S. Thomas Hughes
*Assistant Examiner* — Sarah Simpson
(74) *Attorney, Agent, or Firm* — Nixon Peabody LLP

(57) ABSTRACT

A lancing mechanism is adapted to move between resting, cocking and puncture positions and comprises a lancet holder, a shaft, at least one spring and a mass. The shaft is attached to the lancet holder and has an enlarged end opposite the lancet holder. The spring surrounds at least a portion of the shaft and has first and second portions. The second portion of the spring is attached to the lancet holder. The spring drives the lancing mechanism between the cocking and puncture positions. The mass is located along the spring with the first and second portions of the spring extending on opposite sides of the mass. The mass is distinct from the lancet holder. The first portion dampens the lancing mechanism when moving from the puncture position to the resting position.

19 Claims, 7 Drawing Sheets

U.S. PATENT DOCUMENTS

| | | | |
|---|---|---|---|
| 6,045,567 A * | 4/2000 | Taylor et al. | 606/181 |
| 6,197,040 B1 | 3/2001 | LeVaughn et al. | 606/182 |
| 6,558,402 B1 * | 5/2003 | Chelak et al. | 606/182 |
| 7,238,192 B2 | 7/2007 | List et al. | 606/182 |
| 7,288,102 B2 * | 10/2007 | Griffin et al. | 606/182 |
| 7,905,898 B2 * | 3/2011 | Schraga | 606/181 |
| 2004/0059256 A1 | 3/2004 | Perez | 600/583 |
| 2005/0085840 A1 | 4/2005 | Yi et al. | 606/182 |

FOREIGN PATENT DOCUMENTS

| | | |
|---|---|---|
| EP | 0 898 936 A2 | 3/1999 |
| WO | WO 2005/001418 A2 | 1/2005 |
| WO | WO 2005/077275 A1 | 8/2005 |
| WO | WO 2006/031535 A2 | 3/2006 |

OTHER PUBLICATIONS

International Search Report corresponding to International Patent Application Serial No. PCT/2006/025695, European Patent Office, dated Nov. 10, 2006, 3 pages.

* cited by examiner

SINGLE-PUNCTURE LANCING SYSTEM

CROSS-REFERENCE TO RELATED APPLICATION

This application claims priority to Application No. 60/695,391 filed on Jun. 30, 2005, which is incorporated by reference in its entirety.

FIELD OF THE INVENTION

The present invention relates generally to lancing devices and, more particularly, to a single-puncture lancing mechanism for a lancing device.

BACKGROUND OF THE INVENTION

The quantitative determination of analytes in body fluids is of great importance in the diagnoses and maintenance of certain physiological abnormalities. For example, lactate, cholesterol and bilirubin should be monitored in certain individuals. In particular, determining glucose in body fluids is important to diabetic individuals who must frequently check their blood glucose levels to regulate the glucose intake in their diets.

One method of obtaining a body fluid sample, such as a whole blood sample, is to use a lancing device. The whole blood sample may then be used to determine the glucose concentration of an individual. Existing lancing devices use a lancet to pierce the tissue of the skin, allowing a blood sample to form on the skin's surface. Typically, lancing devices hold the lancet within them when the lancet is not in use, so as to shield the user from injury as well as to assist in preventing or inhibiting contamination.

The whole blood sample is often obtained by piercing the skin of a test subject. In addition to the pain and discomfort inherent with such a puncture, existing lancing devices may cause increased pain to many individuals by failing to properly dampen the lancet after initially piercing the skin. This may result in multiple punctures to the individual's skin, increasing the discomfort to the user. Alternatively, excessive damping can reduce the lancet's force and adversely effect the puncture depth, causing insufficient sample size and the need to lance again.

Additionally, the cost, complexity, effectiveness, and design of lancing devices are important to individual user's. Thus, it would be desirable to have a lancing device and method that address these issues.

SUMMARY OF THE INVENTION

According to one embodiment of the present invention, a lancing mechanism adapted to move between a resting position, a cocking position, and a puncture position is disclosed. The lancing mechanism comprises a lancet holder, a shaft, at least one spring, and a mass. The lancet holder is adapted to receive a lancet. The shaft is attached to the lancet holder and has an enlarged end opposite the lancet holder. The at least one spring surrounds at least a portion of the shaft. The at least one spring has a first portion and a second portion. The second portion of the at least one spring is attached to the lancet holder. The at least one spring is adapted to drive the lancing mechanism between the cocking position and the puncture position. The mass is located along the at least one spring. The first portion and second portion of the at least one spring extend on opposite sides of the mass. The mass is distinct from the lancet holder. The first portion of the at least one spring dampens the lancing mechanism as the lancing mechanism moves from the puncture position to the resting position.

According to another embodiment of the present invention, a lancing device is disclosed. The lancing device comprises a main housing and a movable housing. The main housing forms an inner cavity enclosing a portion of a lancing mechanism. The lancing mechanism is adapted to move between a resting position, a cocking position, and a puncture position. The lancing mechanism includes a lancet holder attached to a shaft having an enlarged end opposite the lancet holder. The main housing further encloses at least one spring surrounding at least a portion of the shaft. The at least one spring has a first portion and a second portion. The second portion of the at least one spring is attached to the lancet holder. The main housing further encloses a mass located along the at least one spring. The first portion and second portion of the at least one spring extend on opposite sides of the mass. The mass is distinct from the lancet holder. The at least one spring being adapted to drive the lancing mechanism between the cocking position and the puncture position. The first portion of the at least one spring damping the lancing mechanism as the lancing mechanism moves from the puncture position to the resting position. The movable housing is adjacent the main housing and is adapted to move from a resting position to a cocking position. The moveable housing forms an inner cavity enclosing a portion of the shaft of the lancing mechanism.

According to yet another embodiment of the present invention, a lancing mechanism adapted to move between a resting position, a cocking position, and a puncture position is disclosed. The lancing mechanism comprises a lancet holder, a shaft, a first and second spring, and a mass. The lancet holder is adapted to receive a lancet. The shaft is attached to the lancet holder and has an enlarged end opposite the lancet holder. The first spring surrounds at least a portion of the shaft. The first spring is attached to the lancet holder and is adapted to drive the lancing mechanism between the cocking position and the puncture position. The second spring has a first end and a second end and is located within the lancet holder. The first end of the spring is attached to the lancet holder. The mass is attached to the second end of the second spring and is located within and distinct from the lancet holder. The second spring is at least partially compressed as the lancing mechanism moves from the cocked position to the puncture position.

The above summary of the present invention is not intended to represent each embodiment, or every aspect, of the present invention. Additional features and benefits of the present invention are apparent from the detailed description and figures set forth below.

BRIEF DESCRIPTION OF THE DRAWINGS

FIG. 1b is a bottom exploded view of the lancing device of FIG. 1a.

DESCRIPTION OF ILLUSTRATED EMBODIMENTS

The present invention is directed to a lancet-release mechanism for incorporation into a stand-alone lancing device or into a lancing device that is incorporated into a meter or similar testing device. The lancing device is adapted to receive a lancet for use in drawing a body fluid from a test subject. The body fluid generally contains at least one analyte that may then be examined to determine its concentration in the body fluid sample.

Lancing devices and lancets may be used to produce a blood or body fluid sample from a test subject. This sample may then be analyzed with a meter and test strip, or similar devices, to determine the concentration of the analyte to be examined. Examples of the types of analytes that may be collected with a lancing device include glucose, lipid profiles (e.g., cholesterol, triglycerides, LDL and HDL), microalbumin, hemoglobin $A_{1C}$, fructose, lactate, or bilirubin.

Figure 1A:
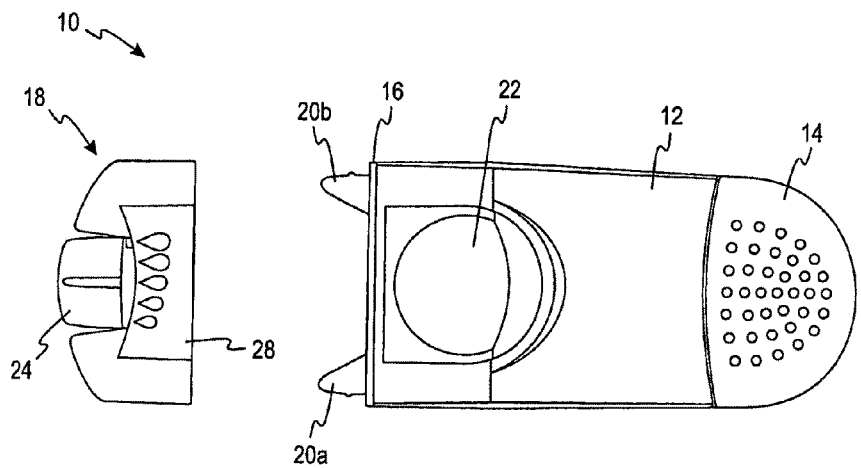
FIG. 1a is a top exploded view of a lancing device, according to one embodiment of the present invention.
Figure 1B:
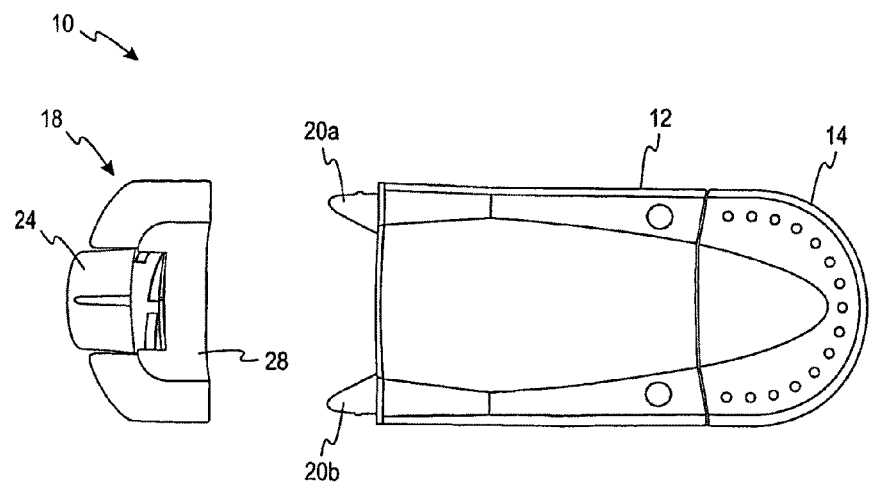
Figure 2:
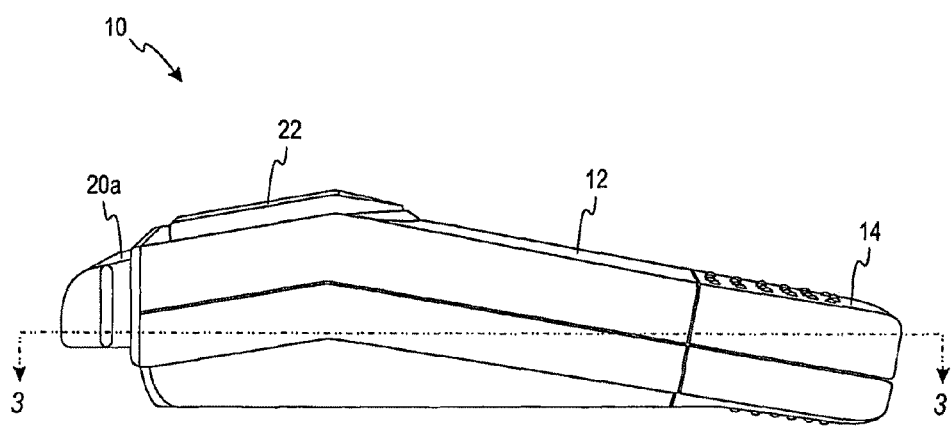
FIG. 2 is a side view of the lancing device of FIGS. 1a-b.

Turning now to the drawings and initially to FIGS. 1-2, a lancing device 10 for obtaining a fluid sample from a test subject is illustrated, according to one embodiment of the present invention. The lancing device 10 has a main housing 12 and a movable housing 14 that is movable relative to the main housing 12. The main housing 12 and the movable housing 14 each forms an inner cavity 24, 26 (FIG. 6a), respectively. An endcap support 16 is connected to the main housing 12 on the testing end of the lancing device 10. An endcap 18 may be removably attached to the endcap support 16. When attached, the endcap 18 is retained on the endcap support 16 by a pair of support arms 20a-b integrally formed with the endcap support 16.

Figure 5:
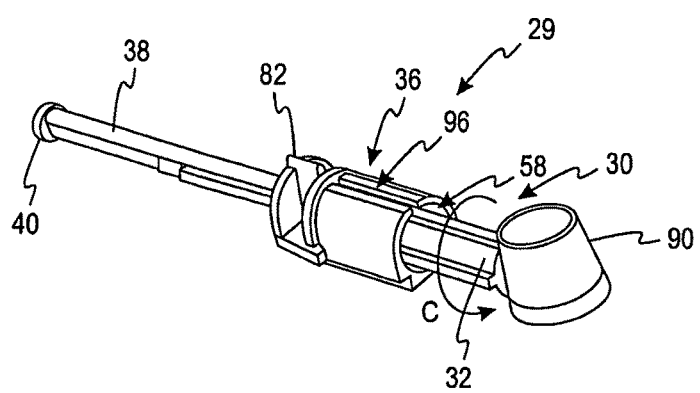
FIG. 5 is a perspective view of a lancing mechanism, according to one embodiment of the present invention.

To use the lancing device 10, the movable housing 14 is pulled away from the main housing 12 to move an internal lancing mechanism 29 (as best illustrated in FIG. 5) to a cocked position, and then a pushbutton 22 is pushed to actuate the lancing mechanism 29 so that the sharp tip of a lancet is forced through an aperture (not shown) in the endcap 18. The lancing device 10 may be provided with a number of different endcaps 18, each having a different width, to facilitate the formation of skin punctures of various depths. Alternatively, the endcap 18 may include an adjustable dial 24 for allowing punctures of different depths to be performed utilizing a single endcap 18.

Figure 3:
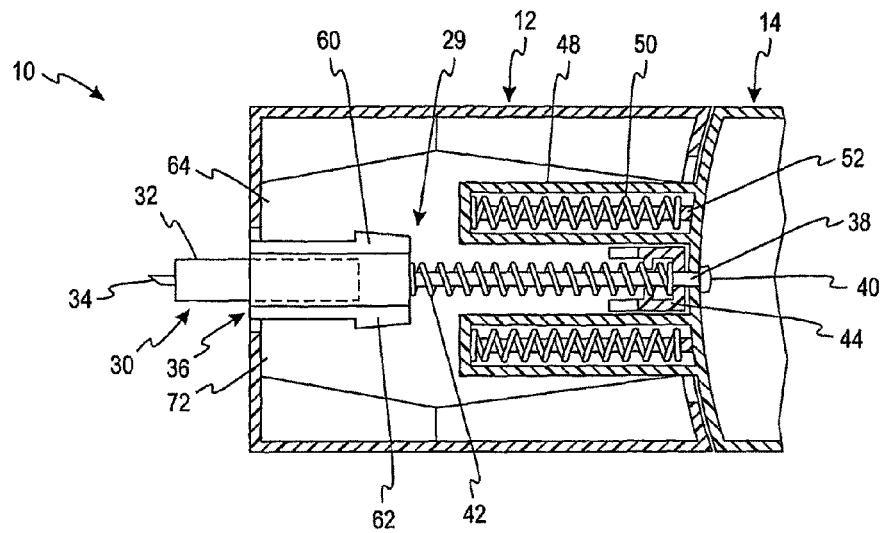
FIG. 3 is a partial, cross-sectional, top view of the lancing device of FIG. 2 in a resting position.
Figure 4:
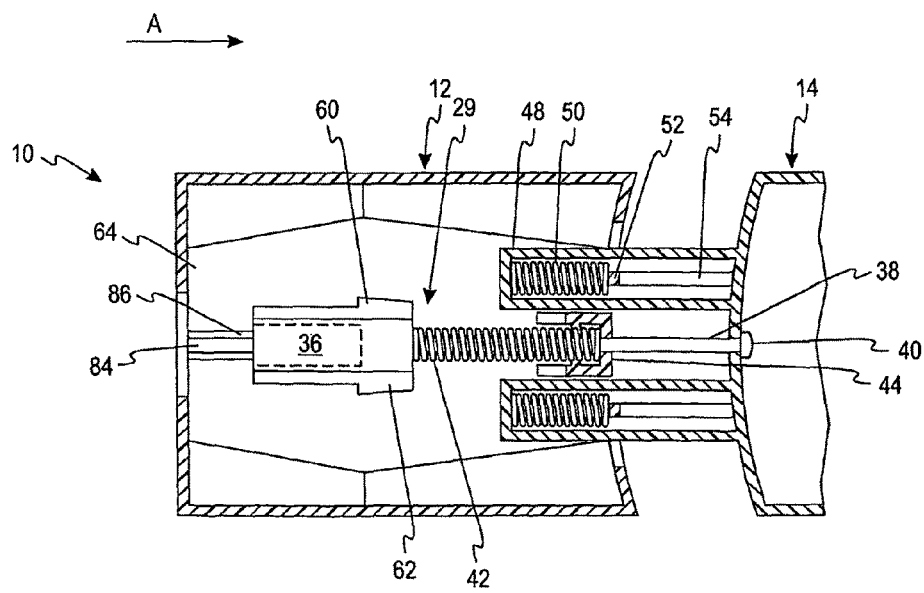
FIG. 4 is a partial, cross-sectional, top view of the lancing device of FIG. 2 in a cocking position.

Turning now to FIG. 3, a cross-sectional view of a portion of the lancing device 10 is illustrated with the endcap 18 and endcap support 16 not shown. A lancet assembly 30 having a lancet body 32 and a lance 34 is received within an internal cylindrical aperture 58 (FIG. 5) formed in a generally cup-shaped lancet holder 36. The lancet holder 36 includes one or more angled stop member. In the illustrated embodiment (FIG. 3), the lancet holder 36 includes two angled stop members 60, 62 that are located on opposite sides of the lancet holder 36. The lancet holder 36 is connected to an elongated shaft 38 by being integrally formed therewith. The shaft 38 has an enlarged end 40 that is supported within the movable housing 14. At least one spring is disposed around the shaft 38 between the lancet holder 36 and a spring stop 44 (see also FIG. 4) integrally formed with the main housing 12. As illustrated in FIGS. 3-4, a single spring 42 is provided according to some embodiments. The spring 42 is a drive spring and is adapted to engage the lancet holder 36.

The movable housing 14 has a pair of elongate spring trays 48 integrally formed therewith. A return spring 50 is disposed within each of the spring trays 48, a first end of each return spring 50 being disposed against an internal surface of the spring tray 48 and a second end of each return spring 50 being disposed against a spring stop 52 integrally formed with the main housing 12. The spring stops 52 extend into the spring trays 48 through an elongate slot 54 (see FIG. 4) formed in the bottom portion of each tray 48.

FIG. 3 illustrates the interior of the lancing device 10 when the lancing device 10 is not in use. In this position, the lancet holder 36 is disposed in a resting position between a puncture position and a cocked position. FIG. 4 illustrates the interior of the lancing device 10 (the lancet assembly 30 is not shown) when the lancet holder 36 is in a cocked position in which the movable housing 14 has been pulled away from the main housing 12.

Referring to FIG. 4, to move the lancet holder 36 from its resting position to its cocked position, the movable housing 14 is pulled away from the main housing 12 in the direction of Arrow A. The movable housing 14 continues to be pulled—against the force of the spring 42—until the angled stop members 60, 62 formed on the lancet holder 36 move past (to the right of as illustrated in FIG. 4) at least one retaining arm (not shown) formed on the housing side of the push button 22. The at least one retaining arm extends into the housing 12. The at least one retaining arm is biased so that it makes contact with one or more of the angled stop members 60, 62 formed on the lancet holder 36. A spring mechanism—for example, an elastically-deformable foam material—may be disposed between the pushbutton 22 and a portion of the main housing 12 to bias the pushbutton 22 to its non-actuated position, wherein the at least one retaining arm is able to engage one or both of the angled stop members 60, 62.

When in that cocked position, movement of the lancet holder 36 in the direction of Arrow B due to the spring 42 is prevented because of the contact between the at least one retaining arm and the angled stop members 60, 62. After the lancet holder 36 is placed in the cocked position, the user allows the return springs 50 to force the movable housing 14 back to its initial position adjacent the main housing 12.

The lancet holder 36 is guided between its resting and cocked positions by a guide rib 82 (FIG. 5) formed on the bottom portion of the lancet holder 36 that rides within a groove 84 formed between a pair of raised guide rails 86 formed in a bottom interior portion of the main housing 12.

To perform a puncture on a test subject's skin, the endcap 18 is attached to the lancing device 10. The lancet holder 36 may be in the cocked position at the time the endcap 18 is attached or may be cocked once the endcap 18 is in position. The endcap 18 is then placed firmly against the skin where the puncture is to be made, and the pushbutton 22 is depressed. Depressing the pushbutton 22 causes the at least one retaining arm (not shown) to release the angled stop members 60, 62 formed on the lancet holder 36. Thus, the lancet holder 36 is no longer prevented from moving in the direction of Arrow B by the contact of the at least one retaining arm with one or both of the angled stop members 60, 62.

Upon release of the lancet holder 36 as described above, the spring 42 will force the lancet holder 36 in the direction of Arrow B until the sharp point of the lance 34 (FIG. 3) passes through the aperture (not shown) in the endcap 18 to make the puncture. When the puncture is made, the spring 42 will be in a stretched position, and after the puncture is made the contraction of the spring 42 will draw the lancet holder 36 back towards its resting position shown in FIG. 3.

Turning now to FIG. 5, a perspective view of the lancing mechanism 29 is illustrated, according to one embodiment of the present invention. The lancet mechanism 29 includes the lancet holder 36 adapted to receive the lancet assembly 30. As illustrated in FIG. 5, the lancet assembly 30 is disposed within the generally cylindrical aperture formed in the lancet holder 36. The lancet assembly 30 is shown with a protective cap 90 that has a portion that is integrally formed with the lancet body 32 and which covers the sharp point of the lance 34. Prior to using the lancing device 10, the lancet body 32 of a new lancet assembly 30 is inserted into the cylindrical aperture disposed in the lancet holder 36, and then the protective cap 90 is twisted off of the lancet assembly 30, in the direction of the Arrow C shown in FIG. 5.

Figure 6A:
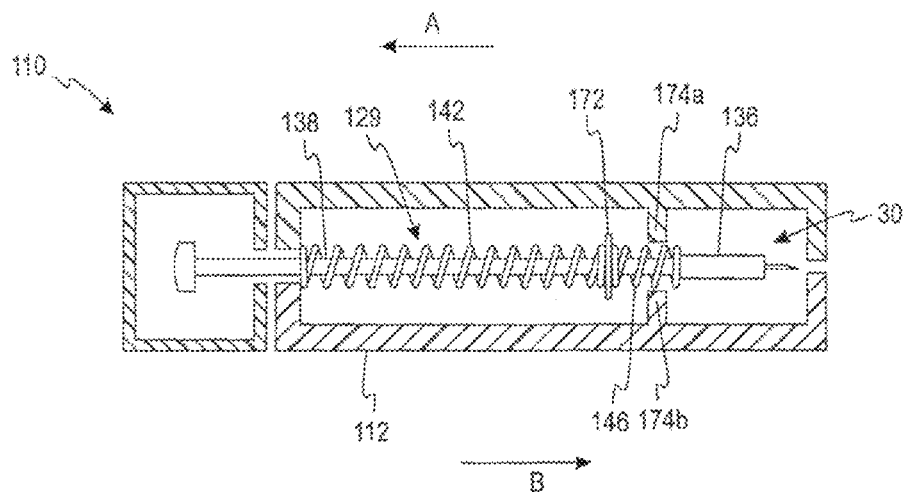
FIG. 6a is a schematic cross-sectional view of a lancing device having a dual-spring firing mechanism, according to one embodiment of the present invention.
Figure 6B:
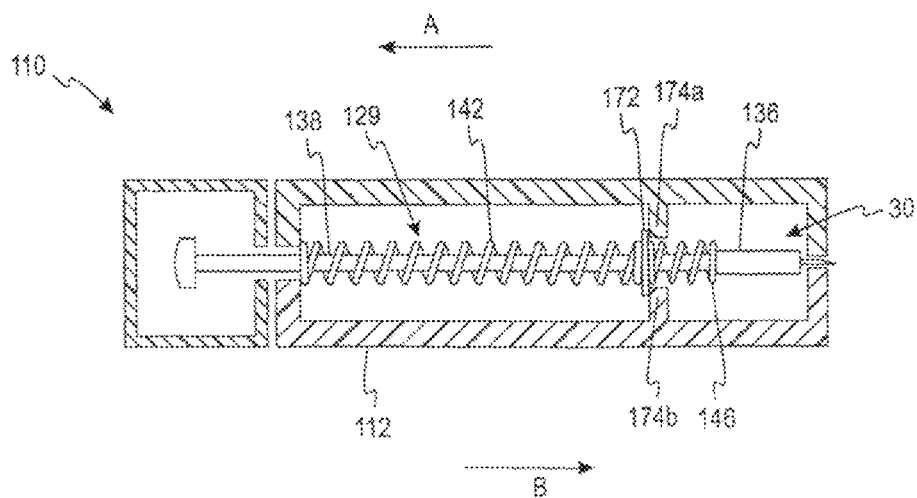
FIG. 6b is a schematic cross-sectional view of the lancing device of FIG. 6a moving from the cocked position to the puncture position.
Figure 6C:
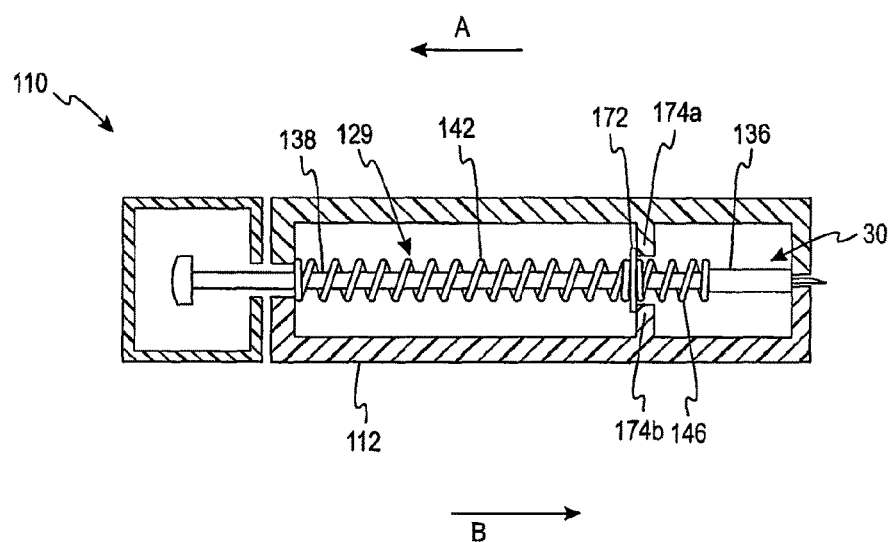
FIG. 6c is a schematic cross-sectional view of the lancing device of FIG. 6a in the puncture position.
Figure 7:
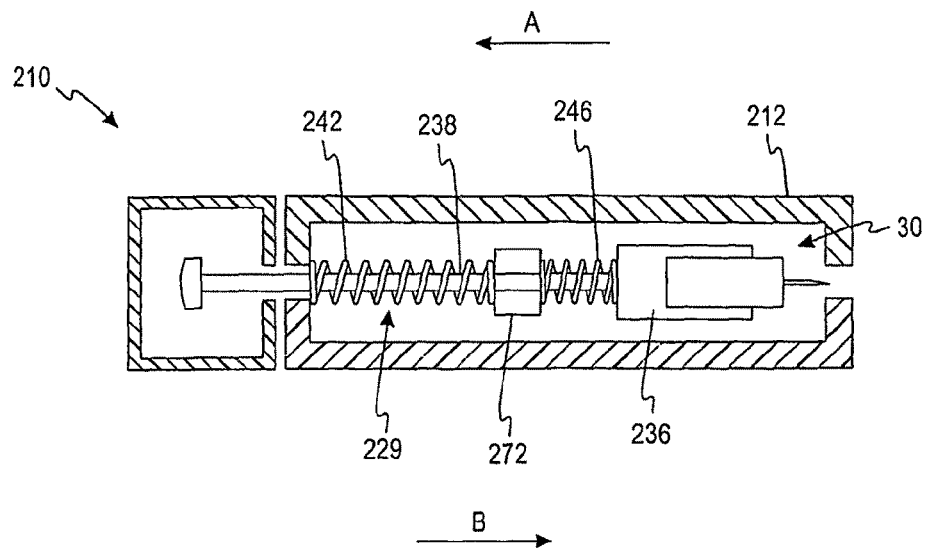
FIG. 7 is a schematic cross-sectional view of a lancing device having a mass located along a spring, according to one embodiment of the present invention.
Figure 8:
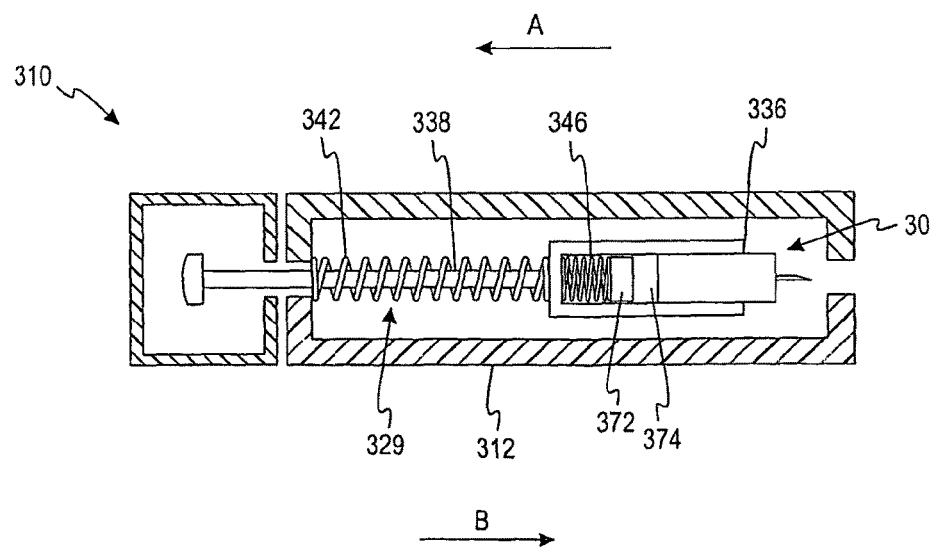
FIG. 8 is a schematic cross-sectional view of a lancing device having a second spring with a mass attached thereto located within a lancet holder, according to one embodiment of the present invention.

Turning now to FIGS. 6-8, a damping system that can be incorporated into the above-described lancing device 10 will be illustrated, according to the various embodiments of the present invention. Such damping systems assist in preventing or inhibiting the spring 42—and its natural tendency to oscillate (due to its being elastically deformable)—from causing a second, unintended skin puncture to be made by the lancet assembly 30. The damping system includes a mass located along the at least one spring of the lancing mechanism 29.

Referring now to FIGS. 6a-6c, a damping system is illustrated that includes a mass, in the form of a plate 172, located between a first spring 142 and a second spring 146. In alternative embodiments, a single spring 42 is used and the mass is located between a first end and a second end of the spring 42. As shown in FIG. 6a, a lancing device 110—incorporating a damping system—is illustrated in the cocked position. In this position, the first spring 142 and the second spring 146 are at least partially compressed. The first spring 142 and the second spring 146 each surround a portion of the shaft 138. The first spring 142 is located between, and attached to, a main housing 112 of the lancing device 110 and the plate 172. The second spring 146 is located between, and attached to, the plate 172 and a lancet holder 136.

When the lancing device 110 is fired by a user, the first spring 142 and the second spring 146 begin to decompress, causing the lancet holder 136 to move in the direction of Arrow B. As the first spring 142 and the second spring 146 continue to decompress, the plate 172 is engaged by a plurality of stop members 174a,b formed on the main housing 112, as illustrated in FIG. 6b. The engagement by the stop members 174a,b inhibits the motion of the plate 172 in the direction of Arrow B. Thus, the first spring 142 is no longer able to decompress and the stop members 174a,b absorb a substantial part of the decompression energy remaining in the first spring 142. Alternatively, the second spring 146 is allowed to further decompress and causes the lancet holder 136 to exit the lancing device 110 and puncture the skin of a test subject with the lancet assembly 30, as illustrated in FIG. 6c.

The stop members 174a,b are positioned so as to allow the first spring 142 to extend further than its free length as the first spring 142 decompresses. Thus, once the plate 172 is engaged by the stop members 174a,b, the first spring 142 has the tendency to naturally recompress in the direction of Arrow A. After the puncture has been made, both the first spring 142 and the second spring 146 recompress because they have both over-extended their free lengths. As this occurs the first spring 142 acts as a dampening spring to the lancing mechanism 129. This dampening assists in preventing or inhibiting a second puncture of the test subject's skin by the lancet assembly 30.

According to other embodiments of the present invention, the first spring 142 and the second spring 146 are a single spring. According to some of these embodiments, the plate 172 is replaced by one or several larger coils within the single spring. These larger coils divide the spring into two separate sections. In these embodiments, both sections can have different spring rates, have different spring diameters, be made from different spring materials, etc.

Turning now to FIG. 7, a lancing device 210 is illustrated having a damping system that includes a mass 272 located between a first spring 242 and a second spring 246. In alternative embodiments, a single spring 42 is used and a mass is molded between a first end and a second end of the spring 42. The first spring 242 and the second spring 246 each surround a portion of the shaft 238. The first spring 242 is located between, and attached to, a main housing 212 of the lancing device 210 and the mass 272. The second spring 246 is located between, and attached to, the mass 272 and a lancet holder 236.

As the lancing device 210 is fired, both the first spring 242 and the second spring 246 begin to decompress. The first spring 242 drives the mass 272, the second spring 246, the lancet holder 236, and the lancet assembly 30 in the direction of Arrow B. The decompression of the second spring 246 drives the lancet holder 236 and the lancet assembly 30 further in the direction of Arrow B while applying a force on the mass 272 in the direction of Arrow A. The force applied by the second spring 246 on the mass 272 should be less than the force applied by the first spring 242 on the mass 272. Thus, the mass 272 should move in the direction of Arrow B as a lancing mechanism 229 moves from the cocked position to the puncture position.

The motion of the lancet assembly 30 and lancet holder 236 can be represented by the equations:

$$(M_1 * a_1) + (C_1 * v_1) + K_1(x_1 - x_2) = 0$$

$$(M_2 * a_2) + (C_2 * v_2) - K_1(x_1 - x_2) + (K_2 * x_2) = 0$$

where, $M_1$=mass of the lancet assembly and holder $x_1$=distance of $M_1$ from its resting position $M_2$=mass of the mass 272 $x_2$=distance of $M_2$ from its resting position $C_1$=frictional coefficient on $M_1$ $v_1$=velocity of $M_1$ $C_2$=frictional coefficient on $M_2$ $v_2$=velocity of $M_2$ $K_1$=spring constant of the second spring 246 $a_1$=acceleration of $M_1$ $K_2$=spring constant of the first spring 242 $a_2$=acceleration of $M_2$ By solving the above equations, the various properties of the first spring 242 and second spring 246, the mass 272, and the lancet holder 236 can be adjusted to reduce the secondary decompressions of the springs. Thus, the repuncturing of a test subject's skin can be prevented or inhibited by adjusting the properties of the various components.

Turning now to FIG. 8, a lancing device 310 is illustrated according to yet another embodiment of the present invention. The lancing device 310 includes a first spring 342 located around a portion of a shaft 338 and attached to a main housing 312 of the lancing device and a lancet holder 336. A second spring 346 is located within a central cavity 374 of the lancet holder 336. The second spring 346 is attached to the lancet holder 346 at one end and, on an opposite end, a mass 372 is attached to the second spring 346. The mass 372 is separate and distinct from the lancet holder 336 and is positioned so as to be able to move within the central cavity 374 between the lancet holder 336 and the lancet assembly 30.

When a lancing mechanism 329 of the lancing device 310 is in the cocked position, the first spring 342 is compressed while the second spring 346 remains in its resting position. As the lancing mechanism 329 moves from the cocked position to the puncture position, the first spring 342 forces the lancet holder 336 in the direction of Arrow B causing the second spring 346 to compress due to the inertia of the mass 372. Depending upon the spring constant of the second spring 346 and the size of the mass 372, the second spring 346 may begin to decompress as the lancing mechanism 329 continues to move towards the puncture position. Alternatively or additionally, the second spring 346 decompresses as the first spring 342 is fully decompressed. The first spring 342, having overshot its free length, then recompresses and the lancet assembly 336 is moved in the direction of Arrow A. The movement of the lancet holder 336—in combination with the decompression of the second spring 346—causes the second spring 346 to overshoot its free length as the first spring 342 is recompressed.

After the first spring 342 has fully recompressed it will again decompress, which, if left undampened, can cause a second puncture of the test subject's skin. However, because the second spring 346 has overshot its free length, as the first spring 342 begins to decompress, the second spring 346 begins to recompress, moving the mass 372 in the direction of Arrow A. The recompression of the second spring 346 dampens the secondary decompression of the first spring, thus preventing or inhibiting a second, unintended puncture.

Alternative Embodiment A

A lancing mechanism adapted to move between a resting position, a cocking position, and a puncture position comprising:
a lancet holder adapted to receive a lancet;
a shaft attached to the lancet holder, the shaft having an enlarged end opposite the lancet holder;
at least one spring surrounding at least a portion of the shaft, the at least one spring having a first portion and a second portion, the second portion of the at least one spring being attached to the lancet holder, the at least one spring being adapted to drive the lancing mechanism between the cocking position and the puncture position; and
a mass located along the at least one spring, the first portion and second portion of the at least one spring extending on opposite sides of the mass, the mass being distinct from the lancet holder,
wherein the first portion of the at least one spring dampens the lancing mechanism as the lancing mechanism moves from the puncture position to the resting position.

Alternative Embodiment B

The lancing mechanism of Alternative Embodiment A wherein the first portion of the at least one spring drives the mass in the direction of the lancet holder as the lancing mechanism moves from the cocking position to the puncture position.

Alternative Embodiment C

The lancing mechanism of Alternative Embodiment A wherein the mass is a plate.

Alternative Embodiment D

The lancing mechanism of Alternative Embodiment C wherein the plate contacts at least one stop feature as the lancing mechanism moves from the cocked position to the puncture position.

Alternative Embodiment E

The lancing mechanism of Alternative Embodiment A wherein the first portion of the at least one spring is a first spring and the second portion of the at least one spring is a second spring.

Alternative Embodiment F

A lancing device comprising:
a main housing forming an inner cavity enclosing a portion of a lancing mechanism, the lancing mechanism being adapted to move between a resting position, a cocking position, and a puncture position, the lancing mechanism including a lancet holder attached to a shaft having an enlarged end opposite the lancet holder, the main housing further enclosing at least one spring surrounding at least a portion of the shaft, the at least one spring having a first portion and a second portion, the second portion of the at least one spring being attached to the lancet holder, the main housing further enclosing a mass located along the at least one spring, the first portion and second portion of the at least one spring extending on opposite sides of the mass, the mass being distinct from the lancet holder, the at least one spring being adapted to drive the lancing mechanism between the cocking position and the puncture position, the first portion of the at least one spring damping the lancing mechanism as the lancing mechanism moves from the puncture position to the resting position; and
a movable housing adjacent the main housing, the movable housing being adapted to move from a resting position to a cocking position, the moveable housing forming an inner cavity enclosing a portion of the shaft of the lancing mechanism.

Alternative Embodiment G

The lancing device of Alternative Embodiment F wherein the mass is a plate.

Alternative Embodiment H

The lancing device of Alternative Embodiment G wherein the plate contacts at least one stop feature formed on the main housing, the plate contacting the at least one stop feature as the lancing mechanism moves from the cocked position to the puncture position.

Alternative Embodiment I

The lancing device of Alternative Embodiment F wherein the mass of the mass is less than the mass of the lancet holder.

Alternative Embodiment J

The lancing device of Alternative Embodiment F wherein the first portion of the at least one spring dampens the lancing mechanism.

Alternative Embodiment K

The lancing device of Alternative Embodiment F wherein the mass is formed along the at least one spring by a molding process.

Alternative Embodiment L

A lancing mechanism adapted to move between a resting position, a cocking position, and a puncture position comprising:
 a lancet holder adapted to receive a lancet;
 a shaft attached to the lancet holder, the shaft having an enlarged end opposite the lancet holder;
 a first spring surrounding at least a portion of the shaft, the first spring being attached to the lancet holder, the first spring being adapted to drive the lancing mechanism between the cocking position and the puncture position;
 a second spring having a first end and a second end, the second spring being located within the lancet holder, the first end of the spring being attached to the lancet holder; and
 a mass attached to the second end of the second spring, the mass being located within and distinct from the lancet holder,
 wherein the second spring is at least partially compressed as the lancing mechanism moves from the cocked position to the puncture position.

Alternative Embodiment M

The lancing device of Alternative Embodiment L wherein the second spring at least partially decompresses as the lancing mechanism moves from the puncture position to the resting position.

Alternative Embodiment N

The lancing device of Alternative Embodiment M wherein the second spring recompresses as the first spring secondarily decompresses.

Alternative Embodiment O

The lancing device of Alternative Embodiment N wherein the recompression of the second spring and the mass dampens the lancing mechanism.

While the invention is susceptible to various modifications and alternative forms, specific embodiments and methods thereof have been shown by way of example in the drawings and are described in detail herein. It should be understood, however, that it is not intended to limit the invention to the particular forms or methods disclosed, but, to the contrary, the intention is to cover all modifications, equivalents and alternatives falling within the spirit and scope of the invention as defined by the appended claims.

The invention claimed is:

1. A lancing mechanism adapted to move between a resting position, a cocking position, and a puncture position comprising:
 a lancet holder adapted to receive a lancet;
 a shaft affixed to the lancet holder, the shaft having an enlarged end opposite the lancet holder;
 at least one spring surrounding at least a portion of the shaft, the at least one spring having a first portion and a second portion, the second portion of the at least one spring being attached to the lancet holder, the at least one spring being adapted to drive the lancing mechanism between the cocking position and the puncture position; and
 a mass located along the at least one spring, the first portion and second portion of the at least one spring being affixed to and extending on opposite sides of the mass, the mass being distinct from the lancet holder and being moveable with respect to the shaft,
 wherein the first portion of the at least one spring dampens the lancing mechanism as the lancing mechanism moves from the puncture position to the resting position.

2. The lancing mechanism of claim 1, wherein the first portion of the at least one spring drives the mass in the direction of the lancet holder as the lancing mechanism moves from the cocking position to the puncture position.

3. The lancing mechanism of claim 1, wherein the mass is a plate.

4. The lancing mechanism of claim 3, wherein the plate contacts at least one stop feature as the lancing mechanism moves from the cocked position to the puncture position.

5. The lancing mechanism of claim 1, wherein the first portion of the at least one spring is a first spring and the second portion of the at least one spring is a second spring.

6. The lancing mechanism of claim 1, wherein the mass is moveable along an axis of the shaft.

7. A lancing device comprising:
 a movable housing; and
 a main housing forming an inner cavity enclosing a portion of a lancing mechanism, the lancing mechanism being adapted to move between a resting position, a cocking position, and a puncture position, the lancing mechanism including a lancet holder affixed to a shaft having an enlarged end opposite the lancet holder, the main housing further enclosing at least one spring surrounding at least a portion of the shaft, the at least one spring having a first portion and a second portion, the second portion of the at least one spring being affixed to the lancet holder, the main housing further enclosing a mass located along the at least one spring, the first portion and second portion of the at least one spring extending on opposite sides of the mass, the mass being distinct from the lancet holder and from the movable housing and being slidably coupled to the shaft, the at least one spring being adapted to drive the lancing mechanism between the cocking position and the puncture position, the first portion of the at least one spring damping the lancing mechanism as the lancing mechanism moves from the puncture position to the resting position,
 wherein the movable housing is adjacent to the main housing, the movable housing being adapted to move from a resting position to a cocking position, the moveable housing forming an inner cavity enclosing a portion of the shaft of the lancing mechanism.

8. The lancing device of claim 7 wherein the mass is a plate.

9. The lancing device of claim 8, wherein the plate contacts at least one stop feature formed on the main housing, the plate contacting the at least one stop feature as the lancing mechanism moves from the cocked position to the puncture position.

10. The lancing device of claim 7, wherein the mass of the mass is less than the mass of the lancet holder.

11. The lancing device of claim 7, wherein the first portion of the at least one spring dampens the lancing mechanism.

12. The lancing device of claim 7, wherein the mass is formed along the at least one spring by a molding process.

13. The lancing device of claim 7, wherein the mass is slidable along an axis of the shaft.

14. A lancing mechanism adapted to move between a resting position, a cocking position, and a puncture position comprising:
- a lancet holder directly coupled to a lancet;
- a shaft attached to the lancet holder, the shaft having an enlarged end opposite the lancet holder;
- a first spring surrounding at least a portion of the shaft, the first spring being attached to the lancet holder, the first spring being adapted to drive the lancing mechanism between the cocking position and the puncture position;
- a second spring having a first end and a second end, the second spring being located within the lancet holder, the first end of the spring being attached to the lancet holder; and
- a mass attached only to the second end of the second spring, the mass being located within and distinct from the lancet holder, wherein the second spring is at least partially compressed as the lancing mechanism moves from the cocked position to the puncture position.

15. The lancing device of claim 14, wherein the second spring at least partially decompresses as the lancing mechanism moves from the puncture position to the resting position.

16. The lancing device of claim 15, wherein the second spring recompresses as the first spring secondarily decompresses.

17. The lancing device of claim 16, wherein the recompression of the second spring and the mass dampens the lancing mechanism.

18. The lancing mechanism of claim 14, wherein the mass is moveable with respect to the shaft.

19. The lancing mechanism of claim 14, wherein the mass is moveable with respect to the lancet holder and the lancet.

* * * * *

UNITED STATES PATENT AND TRADEMARK OFFICE
CERTIFICATE OF CORRECTION

| | | |
|---|---|---|
| PATENT NO. | : 8,460,329 B2 | Page 1 of 1 |
| APPLICATION NO. | : 11/921987 | |
| DATED | : June 11, 2013 | |
| INVENTOR(S) | : Kheiri et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1,084 days.

Signed and Sealed this
Thirtieth Day of December, 2014

Michelle K. Lee
*Deputy Director of the United States Patent and Trademark Office*